US011020492B2

(12) United States Patent
Conway

(10) Patent No.: US 11,020,492 B2
(45) Date of Patent: Jun. 1, 2021

(54) GENE CORRECTION OF SCID-RELATED GENES IN HEMATOPOIETIC STEM AND PROGENITOR CELLS

(71) Applicant: Sangamo Therapeutics, Inc., Richmond, CA (US)

(72) Inventor: Anthony Conway, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 141 days.

(21) Appl. No.: 16/346,237

(22) PCT Filed: Oct. 31, 2017

(86) PCT No.: PCT/US2017/059197
§ 371 (c)(1),
(2) Date: Apr. 30, 2019

(87) PCT Pub. No.: WO2018/081775
PCT Pub. Date: May 3, 2018

(65) Prior Publication Data
US 2019/0262473 A1 Aug. 29, 2019

Related U.S. Application Data

(60) Provisional application No. 62/415,056, filed on Oct. 31, 2016.

(51) Int. Cl.
| | |
|---|---|
| *A61K 48/00* | (2006.01) |
| *A61P 37/06* | (2006.01) |
| *A61K 31/7088* | (2006.01) |
| *A61K 35/545* | (2015.01) |
| *C07K 14/715* | (2006.01) |
| *C12N 9/22* | (2006.01) |
| *C12N 15/86* | (2006.01) |
| *C12N 15/90* | (2006.01) |
| *C12N 15/87* | (2006.01) |
| *C12N 15/85* | (2006.01) |
| *A61K 35/12* | (2015.01) |

(52) U.S. Cl.
CPC ...... *A61K 48/0066* (2013.01); *A61K 31/7088* (2013.01); *A61K 35/545* (2013.01); *A61K 48/00* (2013.01); *A61P 37/06* (2018.01); *C07K 14/7155* (2013.01); *C12N 9/22* (2013.01); *C12N 15/85* (2013.01); *C12N 15/86* (2013.01); *C12N 15/87* (2013.01); *C12N 15/90* (2013.01); *A61K 2035/124* (2013.01); *C12N 2710/16171* (2013.01); *C12N 2710/16632* (2013.01); *C12N 2710/16641* (2013.01); *C12N 2710/16671* (2013.01)

(58) Field of Classification Search
CPC ................................................. A61K 48/0066
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Aiuti, et al., "Lentiviral Hematopoietic Stem Cell Gene Therapy in Patients With Wiskott-Aldrich Syndrome," *Science* 23(341):6148 (2013) doi: 10.1126/science.1233151.

Argast, et al., "I-PPOL and I-CREL Homing Site Sequence Degeneracy Determined by Random Mutagenesis and Sequential In Vitro Enrichment," *J. Mol. Biol.* 280:345-353 (1998).

Ashworth, et al., "Computational Redesign of Endonuclease DNA Binding and Cleavage Specificity," *Nature* 441:656-659 (2006).

Beerli, et al., "Engineering Polydactyl Zinc-Finger Transcription Factors," *Nature Biotechnol.* 20:135-141(2002).

(Continued)

*Primary Examiner* — Scott Long
(74) *Attorney, Agent, or Firm* — Foley & Lardner LLP

(57) ABSTRACT

The present disclosure is in the field of genome engineering, particularly targeted integration of a functional SCID-related genes (e.g., IL2RG, RAG1 and/or RAG2 gene) into an IL2RG gene of a cell for provision of proteins lacking or deficient in SCID.

18 Claims, 2 Drawing Sheets

Specification includes a Sequence Listing.

(56) References Cited

U.S. PATENT DOCUMENTS

| | | |
|---|---|---|
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |
| 8,034,598 B2 | 10/2011 | Miller |
| 8,110,379 B2 | 2/2012 | DeKelver et al. |
| 8,329,986 B2 | 12/2012 | Butler et al. |
| 8,399,218 B2 | 3/2013 | Gupta et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,703,489 B2 | 4/2014 | Wang |
| 8,772,453 B2 | 7/2014 | Paschon et al. |
| 8,871,905 B2 | 10/2014 | Holmes et al. |
| 8,936,936 B2 | 1/2015 | Holmes et al. |
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 9,150,847 B2 | 10/2015 | Rebar |
| 9,200,266 B2 | 12/2015 | Wang |
| 9,206,404 B2 | 12/2015 | Cui et al. |
| 9,394,531 B2 | 7/2016 | Miller et al. |
| 9,394,545 B2 | 7/2016 | Rebar et al. |
| 9,616,090 B2 * | 4/2017 | Conway ............ C07K 14/7155 |
| 9,833,479 B2 * | 12/2017 | Conway ............ A61K 38/1793 |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2007/0117128 A1 | 5/2007 | Smith et al. |
| 2008/0159996 A1 | 7/2008 | Ando et al. |
| 2009/0068164 A1 | 4/2009 | Segal et al. |
| 2010/0218264 A1 | 8/2010 | Cui et al. |
| 2011/0016543 A1 | 1/2011 | Weinstein et al. |
| 2011/0201055 A1 | 8/2011 | Doyon et al. |
| 2011/0265198 A1 | 10/2011 | Gregory et al. |
| 2012/0017290 A1 | 1/2012 | Cui et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0196373 A1 | 8/2013 | Gregory et al. |
| 2014/0335063 A1 | 11/2014 | Cannon et al. |
| 2015/0056705 A1 | 2/2015 | Conway et al. |
| 2015/0064789 A1 | 3/2015 | Paschon et al. |
| 2015/0152436 A1 | 6/2015 | Musunuru et al. |
| 2016/0030477 A1 | 2/2016 | Conway et al. |
| 2018/0087072 A1 | 3/2018 | Miller et al. |

FOREIGN PATENT DOCUMENTS

| | | | |
|---|---|---|---|
| WO | WO 96/06166 A1 | 2/1996 | |
| WO | WO 98/37186 A1 | 8/1998 | |
| WO | WO 98/53057 A1 | 11/1998 | |
| WO | WO 98/53058 A1 | 11/1998 | |
| WO | WO 98/53059 A1 | 11/1998 | |
| WO | WO 98/53060 A1 | 11/1998 | |
| WO | WO 98/54311 A1 | 12/1998 | |
| WO | WO 00/27878 A1 | 5/2000 | |
| WO | WO 01/60970 A2 | 8/2001 | |
| WO | WO 01/88197 A2 | 11/2001 | |
| WO | WO 02/016536 A1 | 2/2002 | |
| WO | WO 02/077227 A2 | 10/2002 | |
| WO | WO 02/099084 A2 | 12/2002 | |
| WO | WO 03/016496 A2 | 2/2003 | |
| WO | WO 07/014275 A2 | 2/2007 | |
| WO | WO 10/079430 A1 | 7/2010 | |
| WO | WO2016019144 * | 2/2016 | ............... C12N 5/10 |

OTHER PUBLICATIONS

Belfort, et al., "Homing Endonucleases: Keeping the House in Order," *Nucleic Acids Research* 25:3379-3388 (1997).
Boch, et al., "Breaking the Code of DNA Binding Specificity of Tal-Type III Effectors," *Science* 326:1509-1512 (2009).
Bonas, et al., "Genetic and Structural Characterization of the Avirulence Gene AVRBS3 From Xanthomonas Campestris PV. Vesicatoria," *Mol. Gen. Genet.* 218:127-136 (1989).
Cavazzana-Calvo, et al., "Gene Therapy of Human Severe Combined Immunodeficiency (SCID)-X1 Disease," *Science* 288:669-672 (2000).
Chevalier, et al., "Design, Activity, and Structure of a Highly Specific Artificial Endonuclease," *Molecular Cell* 10:895-905 (2002).
Choo, et al., "Advances in Zinc Finger Engineering," *Curr. Opin. Struct. Biol.* 10:411-416 (2000).
Christian, et al., "Tal Effector Nucleases Create Targeted DNA Double-Strand Breaks," *Genetics* epub 10.1534/genetics.110.120717.
Cong, et al., "Multiplex Genome Engineering Using CRISPR/CAS Systems," *Sciencexpress* 1/10.1126/science 1231143 (2013).
Dujon, et al., "Mobile Introns: Definition of Terms and Recommended Nomenclature," *Gene* 82:115-118 (1989).
Epinat, et al., "A Novel Engineered Meganuclease Induces Homologous Recombination in Yeast and Mammalian Cells," *Nucleic Acids Research* 31:2952-2962 (2003).
Fagerlund, et al., "The CPF1 CRISPR-CAS Protein Expands Genome-Editing Tools," *Genom Bio* 16(251) 3 pgs. (2015).
Fischer, et al., "Gene Therapy of Severe Combined Immunodeficiencies," *Nature Reviews Immunology* 2:615-621 (2002).
Freeman, et al., "Antimicrobial Prophylaxis for Primary Immunodeficiencies," *Current Opinion in Allergy and Clinical Immunology* 9:525-530 (2009).
Genovese, et al., "Targeted Genome Editing in Human Repopulating Haematopoietic Stem Cells," *Nature* 510:235-240 (2014) doi:10.1038/nature13420.
Gimble, et al., "Substrate Recognition and Induced DNA Distortion by the PI-SCEI Endonuclease, an Enzyme Generated by Protein Splicing," *J. Mol. Biol.* 263:163-180 (1996).
Grover, et al., "Re-Programming DNA-Binding Specificity in Zinc Finger Proteins for Targeting Unique Address in a Genome," *Syst. Synth. Biol.* 4:323-329 (2010).
Guo, et al., "Directed Evolution of an Enhanced and Highly Efficient FOKI Cleavage Domain for Zinc Finger Nucleases," *J. Mol. Biol.* 400(1):96-107 (2010).
Hacein-Bey-Abina, et al., "Sustained Correction of X-Linked Severe Combined Immunodeficiency by Ex Vivo Gene Therapy," *NEJM* 346:1185-1193 (2002).
Hacein-Bey-Abina, et al., "Insertional Oncogenesis in 4 Patients After Retrovirus-Mediated Gene Therapy of SCID-X1," *J. Clin Investigation* 118(9): 3132-3142 (2008).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Heuer, et al., "Repeat Domain Diversity of AVRBS3-Like Genes in Ralstonia Solanacearum Strains and Association With Host Preferences in the Field," *Appl. And Envir. Micro.* 73(13):4379-4384 (2007).
Isalan, et al., "A Rapid, Generally Applicable Method to Engineer Zinc Fingers Illustrated by Targeting the HIV-1 Promoter," *Nat. Biotechnol.* 19:656-660 (2001).
Jansen, et al., "Identification of Genes That are Associated With DNA Repeats in Prokaryotes," *Molecular Microbiology* 43(6):1565-1575 (2002).
Jasin, "Genetic Manipulation of Genomes With Rare-Cutting Endonucleases," *Trends Genet.* 12:224-228 (1996).
Kay, et al., "A Bacterial Effector Acts as a Plant Transcription Factor and Induces a Cell Size Regulator," *Science* 318:648-651 (2007).
Kormann, et al., "Expression of Therapeutic Proteins After Delivery of Chemically Modified MRNA in Mice," *Nature Biotechnology* 29(2):154-157 (2011).

(56) References Cited

OTHER PUBLICATIONS

Kutukculer, et al., "Novel Mutations and Diverse Clinical Phenotypes in Recombinase-Activating Gene 1 Deficiency," *It J of Ped* 38:8 (2012).
Lombardo, et al., "Gene Editing in Human Stem Cells Using Zinc Finger Nucleases and Integrase-Defective Lentiviral Vector Delivery," *Nat. Biotechnology* 25:1298-1306 (2007).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Matthews, et al., "Compound Heterozygous Mutation of RAG1 Leading to Omenn Syndrome," *PLOS One* 10(4):e0121489 (2015).
Moscou, et al., "A Simple Cipher Governs DNA Recognition by TAL Effectors," *Science* 326:1501 (2009).
Olovnikov, et al., "Bacterial Argonaute Samples the Transcriptome to Identify Foreign DNA," *Mol. Cell.* 51(5):594-605 (2013).
Pabo, et al., "Design and Selection of Novel CYS2HIS2 Zinc Finger Proteins," *Ann. Rev. Biochem.* 70:313-340 (2001).
Paques, et al., "Meganucleases and DNA Double-Strand Break-Induced Recombination: Perspectives for Gene Therapy," *Current Gene Therapy* 7:49-66 (2007).
Pardoll, "The Blockade of Immune Checkpoints in Cancer Immunotherapy," *Nat Rev Cancer* 12(4):252 (2012).
Perez, et al., "Establishment of HIV-1 Resistance in CD4+ T Cells by Genome Editing Using Zinc-Finger Nucleases," *Nature Biotechnology* 26:808-816 (2008).
Perler, et al., "Protein Splicing Elements: Inteins and Exteins a Definition of Terms and Recommended Nomenclature," *Nucleic Acids Research* 22:1125-1127 (1994).
Philippe, et al., "Lentiviral Vectors With a Defective Integrase Allow Efficient and Sustained Transgene Expression in Vitro and in Vivo," *Proc. Nat'l. Acad. Sci. USA* 103(47):17684-17689 (2006).

Ran, et al., "In Vivo Genome Editing Using *Staphylococcus aureus* CAS9," *Nature* 520:186-194 (2015).
Schornack, et al., "Gene-For-Gene-Mediated Recognition of Nuclear-Targeted AVRBS3-Like Bacterial Effector Proteins," *J. Plant Physiol.* 163(3):256-272 (2006).
Segal, et al., "Custom DNA-Binding Proteins Come of Age: Polydactyl Zinc-Finger Proteins," *Curr. Opin. Biotechnol.* 12:632-637 (2001).
Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.
Swarts, et al., "DNA-Guided DNA Interference by a Prokaryotic Argonaute," *Nature* 507(7491):258-261 (2014).
Tebas, et al., "Gene Editing of CCR5 in Autologous CD4 T Cells of Persons Infected With HIV," *New Engl. J. Med.* 370(10):901 (2014).
Urnov, et al., "Highly Efficient Endogenous Human Gene Correction Using Designed Zinc-Finger Nucleases," *Nature* 435(7042):646-651 (2005).
Vickers, "Severe Combined Immune Deficiency: Early Hospitalisation and Isolation," Chapter 3, pp. 29-27, ISBN 978-0-470-31986-4 (2009).
Vogel, "A Bacterial Seek-And-Destroy System for Foreign DNA," *Science* 344(6187):972-973 (2014) doi: 10.1126/science.1252962.
Watanabe, et al., "Generation of Interleukin-2 Receptor Gamma Gene Knockout Pigs From Somatic Cells Genetically Modified by Zinc Finger Nuclease-Encoding MRNA," *Plos One* 8(10):e76478 (2013).
Yu, et al., "An Engineered VEGF-Activating Zinc Finger Protein Transcription Factor Improves Blood Flow and Limb Salvage in Advanced-Age Mice," *FASEB J.* 20:479-481 (2006).
Yuan, et al., "Crystal Structure of A. Aeolicus Argonaute, a Site-Specific DNA-Guided Endoribonuclease, Provides Insights Into Risc-Mediated MRNA Cleavage," *Molecular Cell* 19:405-419 (2005) doi: 10.1016/j.molcel.2005.07.011.
Gabriel, et al., "An Unbiased Genome-Wide Analysis of Zinc-Finger Nuclease Specificity," Nature Biotechnology 29(9): 816-823 (2011).

* cited by examiner

ON-TARGET INDELS (%)

|  | 57618-ELD | 57618-nR-5Qabc-ELD | 57618-ELD-K525S | 57618-nR-5Qabc-ELD-K525S |
|---|---|---|---|---|
| 55629-KKR | 55.4875 | 63.7841 | 60.7967 | 47.0317 |
| 55629-nR-5Qabc-KKR | 71.8443 | 73.5897 | 72.6714 | 72.7644 |
| 55629-KKR-K525S | 72.4655 | 70.676 | 50.7455 | 38.1496 |
| 55629-nR-5Qabc-KKR-K525S | 74.6047 | 79.4453 | 65.6144 | 51.5974 |

|  | 57629-ELD | 57629-nR-5Qabc-ELD | 57629-ELD-R416S | 57629-nR-5Qabc-ELD-R416S |
|---|---|---|---|---|
| 57718-KKR | 65.7813 | 72.0865 | 65.3743 | 65.9979 |
| 57718-nR-5Qabc-KKR | 69.3424 | 78.8872 | 73.7846 | 73.8942 |
| 57718-KKR-K525S | 72.6883 | 73.3169 | 69.5977 | 54.9762 |
| 57718-nR-5Qabc-KKR-K525S | 74.4166 | 79.7116 | 72.9522 | 56.1722 |

Figure 1A

ON VS. ∑(OFF-TARGET) INDEL RATIO

| | 57618-ELD | 57618-nR-5Qabc-ELD | 57618-ELD-K525S | 57618-nR-5Qabc-ELD-K525S |
|---|---|---|---|---|
| 55629-KKR | 1.0092068 | 0.870587288 | 6.467183644 | 17.35935481 |
| 55629-nR-5Qabc-KKR | 5.6880245 | 1.777644919 | 37.84574523 | 112.6383901 |
| 55629-KKR-K525S | 6.1197767 | 2.84506634 | 33.13667233 | 58.87283951 |
| 55629-nR-5Qabc-KKR-K525S | 21.007715 | 25.65399768 | 143.8596799 | 155.7422276 |

| | 57629-ELD | 57629-nR-5Qabc-ELD | 57629-ELD-R416S | 57629-nR-5Qabc-ELD-R416S |
|---|---|---|---|---|
| 57718-KKR | 4.2660558 | 4.610585225 | 11.87371499 | 134.1420732 |
| 57718-nR-5Qabc-KKR | 43.551313 | 32.68580899 | 182.9975198 | 172.5290684 |
| 57718-KKR-K525S | 33.694108 | 22.73674254 | 150.8729677 | 323.5797528 |
| 57718-nR-5Qabc-KKR-K525S | 561.63472 | 733.9926335 | 1093.736132 | 331.7909037 |

Figure 1B

GENE CORRECTION OF SCID-RELATED GENES IN HEMATOPOIETIC STEM AND PROGENITOR CELLS

CROSS-REFERENCE TO RELATED APPLICATIONS

This application is a 35 U.S.C. § 371 filing of PCT/US2017/059197, filed Oct. 31, 2017, which claims the benefit of U.S. Provisional Application No. 62/415,056, filed Oct. 31, 2016, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Apr. 23, 2019, is named 83250158SL.txt and is 6,852 bytes in size.

TECHNICAL FIELD

The present disclosure is in the field of genome engineering, particularly targeted modification of an IL2R-gamma (IL2RG) gene.

BACKGROUND

Recombinant transcription factors comprising the DNA binding domains from zinc finger proteins ("ZFPs") or TAL-effector domains ("TALEs") and engineered nucleases including zinc finger nucleases ("ZFNs"), TALENs, CRISPR/Cas nuclease systems, and homing endonucleases that are all designed to specifically bind to target DNA sites have the ability to regulate gene expression of endogenous genes and are useful in genome engineering and gene therapy. See, e.g., U.S. Pat. Nos. 9,394,545; 9,150,847; 9,206,404; 9,045,763; 9,005,973; 8,956,828; 8,936,936; 8,945,868; 8,871,905; 8,586,526; 8,563,314; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 20100218264; 20120017290; 20110265198; 20130137104; 20130122591; 20130177983 and 20130177960 and 20150056705, the disclosures of which are incorporated by reference in their entireties for all purposes. Further, targeted nucleases are being developed based on the Argonaute system (e.g., from *T. thermophilus*, known as 'TtAgo', see Swarts et al (2014) *Nature* 507 (7491): 258-261), which also may have the potential for uses in genome editing and gene therapy.

Nuclease-mediated gene therapy can be used to genetically engineer a cell to have one or more inactivated genes and/or to cause that cell to express a product not previously being produced in that cell (e.g., via transgene insertion and/or via correction of an endogenous sequence). Examples of uses of transgene insertion include the insertion of one or more genes encoding one or more novel therapeutic proteins, insertion of a coding sequence encoding a protein that is lacking in the cell or in the individual, insertion of a wild-type gene in a cell containing a mutated gene sequence, and/or insertion of a sequence that encodes a structural nucleic acid such as shRNA or siRNA. Examples of useful applications of 'correction' of an endogenous gene sequence include alterations of disease-associated gene mutations, alterations in sequences encoding splice sites, alterations in regulatory sequences and targeted alterations of sequences encoding structural characteristics of a protein. Transgene constructs can be inserted by either homology directed repair (HDR) or by end capture during non-homologous end joining (NHEJ) driven processes. See, e.g., U.S. Pat. Nos. 9,045,763; 9,005,973; 7,888,121 and 8,703,489.

Clinical trials using these engineered transcription factors and nucleases have shown that these molecules are capable of treating various conditions, including cancers, HIV and/or blood disorders (such as hemoglobinopathies and/or hemophilias). See, e.g., Yu et al. (2006) *FASEB J.* 20:479-481; Tebas et al (2014) *New Eng Med* 370(10):901. Thus, these approaches can be used for the treatment of diseases.

Severe combined immunodeficiency (SCID) is a heterogeneous group of primary immunodeficiencies comprising at least 11 different conditions (Kutukculer et al (2012) *It J of Ped* 38:8). All patients with SCID are susceptible to infections from common bacteria and viruses as well as opportunistic and fungal pathogens. X-linked severe combined immunodeficiency (X-SCID) is an immunodeficiency disorder in which the body produces very few T cells and natural killer cells. In the absence of T cell help, B cells become defective (Fisher et al. (2002) *Nature Reviews* 2:615-621). It is an X-linked recessive trait such that nearly all patients are male, and stems from a mutated version of the IL2RG gene (also referred to as the "common gamma" gene or "common cytokine receptor gamma chain"), located at xq13.1 on the X-chromosome. The common gamma protein is shared between receptors for IL-2, IL-4, IL-7, IL-9, IL-15 and IL-21, leaving X-SCID patients unable to develop functional T and NK cells. Persons afflicted with X-SCID often have infections very early in life, before three months of age. This occurs due to the decreased amount of immunoglobulin G (IgG) levels in the infant during the three-month stage. This is often followed by viral infections such as pneumonitis, an inflammation of the lung which produces common symptoms such as cough, fever, chills, and shortness of breath. Recurrent eczema-like rashes are also a common symptom. Other common infections experienced by individuals with X-SCID include diarrhea, sepsis, and otitis media. Some other common symptoms that are experienced by X-SCID patients include failure to thrive, gut problems, skin problems, and muscle hypotonia (Vickers *Severe Combined Immune Deficiency: Early Hospitalisation and Isolation* (2009) pp. 29-47. ISBN 978-0-470-31986-4). Without therapeutic and/or environmental intervention, X-SCID is typically fatal during the first year of life (Hacein-Berg-Abina et al, (2002) *NEJM* 346: 1185-1193).

Another type of SCID is related to defects in the recombination activating genes (RAG1, RAG2), where approximately 10% of all SCID cases are tied to RAG1 or RAG2 (Ketukculer, ibid). The protein products of the RAG1 and RAG2 genes (Rag1 and Rag2, respectively) are essential for V(D)J rearrangement in B and T cell receptors, and thus are required for proper development of B cells and T cells and are also thought to be involved in inflammation (see, e.g., U.S. Patent Publication No. 20110016543). Together, Rag1 and Rag2 initiate V(D)J recombination by cleaving DNA to generate double strand breaks which are then repaired by the NHEJ machinery.

Omenn Syndrome is an autosomal recessive variant of SCID with distinctive clinical features of generalized erythodermia, hepatosplenomegaly and lymphadenopathy. Unlike patients with classic SCID, patients with Omenn Syndrome have circulating T cells with an abnormal phenotype: they are typically poorly reactive, oligoclonal, and display cell-surface markers of previous activation. B cells are typically absent or low and IgG levels are generally low while IgE levels are high (Matthews et al (2015) *PLoS One* 10(4):e0121489). Omenn Syndrome is typically caused by mutations in RAG1 or RAG2 although mutations in other genes can also lead to it. Generally, hypomorphic RAG mutations, sometimes in combination with RAG null mutations, lead to Omenn Syndrome (Matthews, ibid).

Currently, there are three types of treatments available for SCID patients, namely, the use of medication, sterile environments, and intravenous immunoglobulin therapy (IVIG). First, antibiotics or antivirals are administered to control opportunistic infections, such as fluconazole for candidiasis, and acyclovir to prevent herpes virus infection (Freeman et al. *Current Opinion in Allergy and Clinical Immunology* (2009) 9 (6). 525-530). In addition, the patient can also undergo intravenous immunoglobulin (IVIG) supplementation. However, the IVIG is expensive, in terms of both time and money. In addition, the aforementioned treatments only serve to prevent opportunistic infections, and are by no means a cure for X-SCID or other SCID disorders.

At present, bone marrow transplantation (BMT) is the standard curative procedure and results in a full immune reconstitution, if an appropriate donor can be identified and if the engraftment is successful. A bone marrow transplant requires an acceptable human leukocyte antigen (HLA) match between the donor and the recipient. As the array of HLA molecules is different between individuals, cells of the immune system can utilize the HLA apparatus to distinguish self from foreign cells. A BMT can be allogeneic (donor and recipient are different people) or autologous (donor and recipient are the same person). An autologous BMT therefore has a full HLA match, whereas, a match for an allogenic BMT is more complicated. In standard practice, an allogenic graft is better when all 6 of the known major HLA antigens are the same—a 6 out of 6 match. Patients with a 6/6 match have a lower chance of graft-versus-host disease, graft rejection, having a weak immune system, and getting serious infections. For bone marrow and peripheral blood stem cell transplants, sometimes a donor with a single mismatched antigen is used—a 5 out of 6 match. Therefore, a BMT may result in a full immune reconstitution and thus be curative in an X-SCID patient, but potential complications limit efficacy and widespread use. For patients with Omenn Syndrome, BMT is also the preferred method of treatment however Omenn Syndrome patients have a higher rate of mortality following BMT than other SCID patients.

Previous gene therapy clinical trials for X-SCID patients have used retroviral vectors comprising a wild type IL2RG gene (Cavazzana-Calvo et al. (2000) *Science* 288(5466): 669-72). Retroviral vectors randomly integrate into the host genome, however, and thus can cause insertional oncogenesis in patients when integration occurs in proto-oncogenes (Hacein-Bey-Abina et al. (2008) *J. Clin Investigation* 118 (9):3132-42). The majority of patients undergoing this therapy developed leukemia as a result of this insertional oncogenesis, thus this method is not a safe and effective therapy.

The development of integrase-deficient lentiviral vectors (IDLV) (Philippe et al. (2006) *Proc. Nat'l Acad. Sci.* 103 (47):17684-9), or IDLV, has facilitated further investigation of gene correction of IL2RG for X-SCID due to its inability to integrate into the host genome. The ability of zinc finger nucleases (ZFNs), transcription activator-like effector nucleases (TALENs), CRISPR/Cas systems and TtAgo to target a specific region of DNA, introduce a targeted double stranded break, which then facilitates targeted integration of an introduced transgene makes this genome editing technology highly attractive in the development of a potential curative treatment.

To this end, investigators have targeted exon 5 of the endogenous IL2RG locus for ZFN cleavage and subsequent TI of IDLV-delivered corrective IL2RG cDNA in hematopoietic stem and progenitor cells (HSPCs). See, e.g., U.S. Pat. Nos. 7,888,121 and 7,951,925; Lombardo et al. (2007) *Nat Biotech* 25(11):1298-306; Genovese et al. (2014) *Nature* 510(7504):235-40. However, these methods may have potential disadvantages in that introducing a transgene in the middle of an exon creates a partially transcribed region upstream of the introduced transgene, which may interfere with the activity of the introduced corrective gene. Furthermore, the delivered episomal transgene may still be able to randomly integrate into the genome if another viral integrase is present in the cell. Immunosuppressed patients (such as all X-SCID patients are) might have activation of endogenous retroviruses, thus barring patients who are also HIV positive from receiving virally delivered gene therapy for X-SCID treatment. IL2RG and RAG targeted nucleases are also described in 20160030477.

However, there remains a need for additional methods and compositions for IL2RG gene correction and donor delivery for treatment and/or prevention of SCID.

SUMMARY

The present invention describes compositions and methods for use in gene therapy and genome engineering. Specifically, the methods and compositions described relate to nuclease-mediated genomic modification (e.g., one or more insertions and/or deletions) of an endogenous IL2RG gene (mutant or wild-type). The genomic modification(s) may comprise insertions and/or deletions ("indels") that (i) inactivate the target gene (e.g., via NHEJ following cleavage of the gene by the nuclease); (ii) lead to targeted insertion of a transgene (donor) including protein-encoding sequence, for example, to supply a protein that is lacking or deficient in a subject with a SCID, and/or (iii) perform targeted insertion of a corrective donor (e.g., a sequence that restores functional IL2RG expression in a mutant IL2RG endogenous gene). In certain embodiments, targeted integration into IL2RG of corrective SCID-related gene cassette (e.g., hematopoietic stem cell with mutant versions of the SCID-related gene) using highly IL2RG-specific DNA binding proteins (ZFNs, TALENs, CRISPR/Cas systems). The SCID-related gene cassettes (e.g., functional IL2RG transgene) integrated into the targeted IL2RG gene may be carried on a viral or non-viral vector (e.g., adeno-associated viral (AAV)) and/or may be integrated using one or more nucleases.

In one aspect, disclosed herein are methods and compositions for targeted modification of an IL2RG gene using one or more nucleases. Nucleases, for example engineered meganucleases, zinc finger nucleases (ZFNs) (the term "a ZFN" includes a pair of ZFNs), TALE-nucleases (TALENs including fusions of TALE effectors domains with nuclease domains from restriction endonucleases and/or from meganucleases (such as mega TALEs and compact TALENs)) (the term "a TALEN" includes a pair of TALENs), Ttago system and/or CRISPR/Cas nuclease systems are used to cleave DNA at an IL2RG gene locus in the cell. The IL2RGgene may be inactivated following cleavage (e.g., by insertions and/or deletions ("indels")) and/or by targeted insertion of a donor transgene. The donor transgene may be via homology directed repair (HDR) or non-homology repair mechanisms (e.g., NHEJ donor capture). The nucleases described herein can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase. Any of the nucleases described herein (e.g., ZFNs, TALENs, CRISPR/Cas etc.) may target an intron (e.g., intron 1 or 2) of an IL2RG gene, for instance the target sequences shown Table 2, including for example a target site comprising 9 to 20 or more (9, 10, 11, 12, 13, 14, 15, 16, 17, 18, 19, 20 or more) contiguous or non-contiguous amino acids of SEQ ID Nos:1 or 2.

In one aspect, described herein is a non-naturally occurring zinc-finger protein (ZFP) that binds to a target site in an IL2RG gene in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases and may be wild-type or engineered (mutant). In one embodiment, the cleavage half-domains are derived from a Type IIS restriction endonuclease (e.g., Fok I). In certain embodiments, the zinc finger domain a zinc finger protein with the recognition helix domains ordered as shown in a single row of Table 1. Nucleases comprising these zinc finger proteins may include any linker sequence (e.g., linking it to the cleavage domain) and any cleavage domain (e.g., a dimerization mutant such as an ELD mutant; a FokI domain having mutation at one or more of 416, 422, 447, 448, and/or 525; and/or catalytic domain mutants that result in nickase functionality). See, e.g., U.S. Pat. Nos. 8,703,489; 9,200,266; 8,623,618; and 7,914,796 and U.S. application Ser. No. 15/685,580. In certain embodiments, the ZFP of the ZFN binds to a target site of 9 to 18 or more nucleotides within the sequence shown in SEQ ID NO:1 or 2.

In another aspect, described herein is a Transcription Activator Like Effector (TALE) protein that binds to target site (e.g., a target site comprising at least 9 or 12 (e.g., 9 to 20 or more) nucleotides of a target sequence as shown in Table 2, SEQ ID NO:1 or 2) in an IL2Rγ gene in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases (meganuclease). In one embodiment, the cleavage half-domains are derived from a Type IIS restriction endonuclease (e.g., Fok I). In other embodiments, the cleavage domain is derived from a meganuclease, which meganuclease domain may also exhibit DNA-binding functionality.

In another aspect, described herein is a CRISPR/Cas system that binds to target site in an IL2Rγ gene in a genome, wherein the CRISPR/Cas system comprises one or more engineered single guide RNA or a functional equivalent, as well as a Cas9 nuclease. In certain embodiments, the single guide RNA (sgRNA) binds to a sequence comprising 9, 12 or more contiguous nucleotides of a target site as shown in Table 2 (SEQ ID NO:1 or 2).

The nucleases (e.g., ZFN, CRISPR/Cas system, Ttago and/or TALEN) as described herein may bind to and/or cleave the region of interest in a coding or non-coding region within or adjacent to the ILR2γ gene, such as, for example, a leader sequence, trailer sequence or intron, or within a non-transcribed region, either upstream or downstream of the coding region.

In another aspect, described herein is a polynucleotide encoding one or more nucleases (e.g., ZFNs, CRISPR/Cas systems, Ttago and/or TALENs described herein). The polynucleotide may be, for example, mRNA. In some aspects, the mRNA may be chemically modified (See e.g. Kormann et al, (2011) *Nature Biotechnology* 29(2): 154-157).

In another aspect, described herein is a ZFN, CRISPR/Cas system, Ttago and/or TALEN expression vector comprising a polynucleotide, encoding one or more nucleases (e.g., ZFNs, CRISPR/Cas systems, Ttago and/or TALENs) as described herein, operably linked to a promoter. In one embodiment, the expression vector is a viral vector (e.g., an AAV vector). In one aspect, the viral vector exhibits tissue specific tropism.

In another aspect, described herein is a host cell comprising one or more nuclease (e.g., ZFN, CRISPR/Cas systems, Ttago and/or TALEN) expression vectors.

In another aspect, pharmaceutical compositions comprising an expression vector as described herein are provided. In some embodiments, the pharmaceutical composition may comprise more than one expression vector. In some embodiments, the pharmaceutical composition comprises a first expression vector comprising a first polynucleotide, and a second expression vector comprising a second polynucleotide. In some embodiments, the first polynucleotide and the second polynucleotide are different. In some embodiments, the first polynucleotide and the second polynucleotide are substantially the same. The pharmaceutical composition may further comprise a donor sequence (e.g., a transgene encoding a protein lacking or deficient in a disease or disorder such as an LSD or a hemophilia). In some embodiments, the donor sequence is associated with an expression vector.

In some embodiments, a fusion protein comprising a IL2Rγ DNA-binding domain (e.g., zinc finger protein or TALE or sgRNA or meganuclease) and a wild-type or engineered cleavage domain or cleavage half-domain are provided.

The nucleases described herein may bind to and/or cleave an IL2RG gene within the coding region of the gene or in a non-coding sequence within or adjacent to the gene, such as, for example, a leader sequence, trailer sequence or intron, or within a non-transcribed region, either upstream or downstream of the coding region. In certain embodiments, the nucleases bind to a target site of 9-20 or more nucleotides within the IL2RG sequences shown in Table 2.

In another aspect, described herein are compositions comprising one or more of the nucleases (e.g., ZFNs, TALENs, TtAgo and/or CRISPR/Cas systems) described herein, including a nuclease comprising a DNA-binding molecule (e.g., ZFP, TALE, sgRNA, etc.) and a nuclease (cleavage) domain. In certain embodiments, the composition comprises one or more nucleases in combination with a pharmaceutically acceptable excipient. In some embodiments, the composition comprises two or more sets (pairs) of nucleases, each set with different specificities. In other aspects, the composition comprises different types of nucleases. In some embodiments, the composition comprises polynucleotides encoding IL2RG-nucleases, while in other embodiments, the composition comprises IL2RG-specific nuclease proteins. In still further embodiments, the composition comprises one or more donor molecules, for example donors that encode a functional IL2RG, Rag1 and/or Rag2 protein(s), including any functional fragment thereof. In preferred embodiments, the donor comprises a partial IL2RG and/or RAG (e.g., RAG1 or RAG2) gene. Also preferred is a donor comprising a cDNA comprising exons 2 through 8 of the wild type IL2RG gene. Another preferred donor is a cDNA comprising exon 3 of a wild type RAG (RAG1 and/or RAG2) gene. In other aspects, the donor comprises a corrective sequence that is integrated into a mutant IL2RG gene in a cell such that the cell expresses of functional IL2RG.

In another aspect, described herein is a polynucleotide encoding one or more nucleases or nuclease components (e.g., ZFNs, TALENs, TtAgo or nuclease domains of the CRISPR/Cas system) described herein. The polynucleotide may be, for example, mRNA or DNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 20120195936). In another aspect, described herein is a nuclease expression vector comprising a polynucleotide, encoding one or more ZFNs, TALENs, TtAgo or CRISPR/Cas systems described herein, operably linked to a promoter. In one embodiment, the expression vector is a viral vector, for example an AAV vector.

In another aspect, described herein is a host cell comprising one or more nucleases, one or more nuclease expression vectors, and/or one or more donors as described herein. In certain embodiments, the host cell includes a mutant version of one or more SCID-related genes (e.g., IL2RG gene) such that integration of the SCID-related gene cassette mediated by the IL2RG-specific nuclease provides a functional version of the protein lacking or deficient in the cell by correcting the native mutant version. The host cell may be stably transformed or transiently transfected or a combination thereof with one or more nuclease expression vectors. In one embodiment, the host cell is a T-cell or a stem cell, for example a hematopoietic stem cell or an induced pluripotent stem cell. In other embodiments, the one or more nuclease expression vectors express one or more nucleases in the host cell. In another embodiment, the host cell may further comprise an exogenous polynucleotide donor sequence (e.g., encoding an IL2RG or Rag protein). In any of the embodiments, described herein, the host cell can comprise an embryo cell, for example a one or more mouse, rat, rabbit or other mammal cell embryo (e.g., a non-human primate). In some embodiments, the host cell comprises a tissue. Also described are cells or cell lines descended from the cells described herein, including pluripotent, totipotent, multipotent or differentiated cells comprising a modification (e.g., integrated donor sequence) in an intron of an endogenous IL2RG gene (e.g., intron 1 of an endogenous IL2RG gene). In certain embodiments, described herein are differentiated cells as described herein comprising a modification (e.g., integrated donor sequence) in an intron of an endogenous IL2RG gene (e.g., intron 1 of an endogenous IL2RG), which differentiated cells are descended from a stem cell as described herein.

In another aspect, described herein is a method for cleaving an IL2RG gene in a cell, the method comprising: (a) introducing, into the cell, one or more polynucleotides encoding one or more nucleases that target one or more IL2RG gene under conditions such that the nuclease(s) is(are) expressed and the one or more IL2RG genes are cleaved.

In certain embodiments, following cleavage by the nuclease, a genomic sequence in the target IL2RG gene is cleaved, for example using a nuclease (or vector encoding the nuclease) as described herein and a "donor" sequence inserted into the gene following targeted cleavage with the ZFN, TALEN, TtAgo or CRISPR/Cas system such that the donor sequence is expressed in the cell. The donor sequence may encode a functional IL2RG or Rag protein. In some embodiments, the donor sequence comprises a partial IL2RG and/or RAG (RAG1 or RAG2) gene sequence. In preferred embodiments, the donor comprises a partial cDNA of the IL2RG gene sequence comprising exons 2 through 8, or a full cDNA of the RAG1 gene comprising exon 3, or a full cDNA of the RAG2 gene comprising exon 3. Furthermore, the donor sequence may be present in the nuclease delivery system (e.g., non-viral vector or viral vector), present in a separate delivery mechanism (e.g., nuclease delivered in mRNA form and donor delivered using viral vector such as AAV) or, alternatively, may be introduced into the cell using a separate and/or different nucleic acid delivery mechanism. Insertion of a donor nucleotide sequence into the IL2RG locus can result in the expression of the transgene under control of the endogenous IL2RG genetic control elements, respectively. In some aspects, insertion of the transgene of interest results in expression of an intact exogenous protein sequence and lacks any IL2RG-encoded amino acids. In other aspects, the expressed exogenous protein is a fusion protein and comprises amino acids encoded by the transgene and by the IL2RG gene. In some instances, the IL2RG sequences will be present on the amino (N)-terminal portion of the exogenous protein, while in others, the IL2RG sequences will be present on the carboxy (C)-terminal portion of the exogenous protein. In other instances, IL2RG sequences will be present on both the N- and C-terminal portions of the exogenous protein. The donor may also be a "corrective" sequence that is integrated into a mutant endogenous IL2RG gene that does not express the IL2RG protein (or expresses at levels below normal wild-type levels) such that expression of the IL2RG is restored.

In some embodiments, the invention describes methods and compositions that can be used to express a transgene under the control of the IL2RG promoter in vivo. In some aspects, the transgene may encode a therapeutic protein of interest. The transgene may encode a protein such that the methods of the invention can be used for protein replacement. In some aspects, the transgene encodes an IL2RG or Rag (e.g., Rag1 or Rag2) protein that treats and/or prevents SCID or Omenn Syndrome. In other aspects, the transgene comprises a partial IL2RG and/or RAG (RAG1 or RAG2), gene sequence.

In some embodiments, the nuclease target and/or cleavage site is in an intron of the IL2RG gene such that a transgene (e.g., IL2RG-, Rag1 or Rag2-encoding transgene) is integrated into an intronic region of IL2RG, for example into intron 1, intron 2 or intron 2, respectively. The transgene may be under the control of another endogenous or exogenous promoter of interest in vivo or in vitro, which exogenous promoter drives expression of the transgene. In preferred embodiments, the IL2RG, transgene comprises a cDNA comprising exons 2 through 8 of IL2RG, and further comprises a splice acceptor site such that upon integration and expression, the endogenous IL2RG exon 1 are linked to the transgenic exons 2-8 sequences such that a wild type IL2RG protein is produced and treats or prevents X-SCID or Omenn Syndrome.

In another aspect, a method of modifying an endogenous gene is described, the method comprising administering to the cell one or more polynucleotides encoding one or more nucleases (e.g., ZFNs, TALENs, TtAgo, CRISPR/Cas system) in the presence of one or more donor sequence encoding an IL2RG or Rag protein, such that the donor is integrated into the endogenous gene targeted by the nuclease. Integration of one or more donor molecule(s) occurs via homology-directed repair (HDR) or by non-homologous end joining (NHEJ) associated repair. In certain embodiments, one or more pairs of nucleases are employed, which nucleases may be encoded by the same or different nucleic acids.

In yet another aspect, provided herein is a cell (e.g., T-cell or stem cell) comprising an IL2RG, RAG1 and/or RAG2 transgene which has been integrated into the genome in a targeted manner using a nuclease as described herein. In certain embodiments, the cell is made by the methods described herein. In other preferred embodiments, the IL2RG, RAG1 or RAG2 transgene is integrated into an intronic region of IL2RG (e.g., intron 1, including but not limited into or within 5-10 base pairs of a sequence as shown in any of SEQ ID NOs:1 or 2). The cells comprising the integrated IL2RG, and/or RAG (RAG1 or RAG2) transgene may express the transgene from an endogenous promoter (e.g., the IL2RG promoter, respectively) or, alternatively, the transgene may include regulatory and control elements such as exogenous promoters that drive expression of the IL2RG, RAG1 or RAG2 transgene. In certain embodiments, the cells comprising an IL2RG transgene do not include any viral vector sequences integrated into the genome.

In any of the methods and compositions described herein, the cells may be any eukaryotic cell. In certain embodiments, the cells are T-cells or stem cells. In other embodiments, the cells are patient-derived, for example autologous CD34+ (hematopoietic) stem cells (e.g., mobilized in patients from the bone marrow into the peripheral blood via granulocyte colony-stimulating factor (GCSF) administration). The CD34+ cells can be harvested, purified, cultured, and the nucleases and/or IL2RG donor (e.g., an adenoviral vector donor) introduced into the cell by any suitable method.

In another aspect, the methods and compositions of the invention provide for the use of compositions (nucleases, pharmaceutical compositions, polynucleotides, expression vectors, cells, cell lines and/or animals such as transgenic animals) as described herein, for example for use in treatment of a SCID-related disorder and/or drug screening. In certain embodiments, these compositions are used in the screening of drug libraries and/or other therapeutic compositions (i.e., antibodies, structural RNAs, etc.) for use in treatment of X-SCID or Omenn Syndrome. Such screens can begin at the cellular level with manipulated cell lines or primary cells, and can progress up to the level of treatment of a whole animal (e.g., human). Thus, in certain aspects, described herein is a method of treating and/or preventing X-SCID or Omenn Syndrome in a subject in need thereof, the method comprising administering one or more nucleases, polynucleotides and/or cells as described herein to the subject. The methods may be ex vivo or in vivo. In certain embodiments, a cell as described herein (e.g., a cell comprising an IL2RG, RAG1 or RAG2 transgene) is administered to the subject. In any of the methods described herein, the cell may be a stem cell derived from the subject (patient-derived stem cell).

In any of the compositions and methods described herein, the nucleases are introduced in mRNA form and/or using one or more non-viral or viral vector(s). In certain embodiments, the nuclease(s) are introduced in mRNA form. In other embodiments, the IL2RG and/or RAG (RAG1 or RAG2) transgene is introduced using a viral vector, for instance an adeno-associated vector (AAV) including AAV1, AAV3, AAV4, AAV5, AAV6, AAV8, AAV 8.2, AAV9, AAV rh10, AAV2/8, AAV2/5 and AAV2/6, or via a lentiviral or integration-defective lentiviral vector, and the nuclease(s) is(are) introduced in mRNA form. In still further embodiments, the nuclease(s) and donors are both introduced using one or more viral or non-viral vectors. The nuclease and donor may be carried on the same vector, on different vectors of the same type or on different vectors of different types. In certain embodiments, the nuclease(s) is(are) introduced in mRNA form (e.g., via electroporation) and the donor is introduced using an AAV (e.g., AAV2/6), lentivirus or integration defective lentivirus. In certain embodiments, the donor is introduced as single-stranded DNA.

The nuclease(s) and donors may be introduced concurrently or in order. When introduced sequentially, any time period (e.g., seconds to hours) may elapse between administration of the nucleases and donors. In certain embodiments, the donors are introduced and after 12-36 hours (or any time therebetween), the nuclease are introduced into the cell. In certain embodiments, the modified cells are incubated for hours to days (or any time therebetween) and then are aliquoted and frozen.

Any cell can be modified using the compositions and methods of the invention, including but not limited to prokaryotic or eukaryotic cells such as bacterial, insect, yeast, fish, mammalian (including non-human mammals), and plant cells. In certain embodiments, the cell is an immune cell, for example a T-cell (e.g., CD4+, CD3+, CD8+, etc.), a dendritic cell, a B cell or the like. In other embodiments, the cell is a pluripotent, totipotent or multipotent stem cell, for example an induced pluripotent stem cell (iPSC), hematopoietic stem cells (e.g., CD34+), an embryonic stem cell or the like. In any of the methods or compositions described herein, the cell containing the IL2RG-encoding transgene can be a stem or progenitor cell. Specific stem cell types that may be used with the methods and compositions of the invention include embryonic stem cells (ESC), induced pluripotent stem cells (iPSC) and hematopoietic stem cells (e.g., CD34+ cells). The iPSCs can be derived from patient samples and from normal controls wherein the patient derived iPSC can be mutated to the normal or wild type gene sequence at the gene of interest, or normal cells can be altered to the known disease allele at the gene of interest. Similarly, the hematopoietic stem cells can be isolated from a patient (e.g., a SCID patient with a mutant form of one or more SCID-related genes such as IL2RG and/or RAG) or from a donor. These cells are then engineered to express functional SCID-related protein(s) such as IL2RG or Rag (e.g., Rag1 or Rag2), expanded and then reintroduced into the patient. In certain embodiments, the cell is a patient derived hematopoietic stem cell. In other embodiments, the cell is a COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells.

A kit, comprising the nucleic acids, proteins and/or cells of the invention, is also provided. The kit may comprise nucleic acids encoding the nucleases, (e.g. RNA molecules or ZFN, TALEN, TtAgo or CRISPR/Cas system encoding genes contained in a suitable expression vector), or aliquots of the nuclease proteins, donor molecules, suitable stemness modifiers, cells, instructions for performing the methods of the invention, and the like.

These and other aspects will be readily apparent to the skilled artisan in light of disclosure as a whole.

BRIEF DESCRIPTION OF THE DRAWINGS

FIGS. 1A and 1B show the results of activity of IL2RG-specific ZFNs in CD34+ cells with the indicated engineered FokI domains including dimerization mutants (ELD and KKR), ZFP phosphate contact mutants (nR-5Qabc), as well as FokI phosphate contact mutants (R416S and K525S) at intended (on) and off-target sites. See, e.g., U.S. Pat. No. 8,623,618 and U.S. application Ser. No. 15/685,580. FIG. 1A shows the percent indels ("% indels") at on-target (intended) sites using the indicated pairs. FIG. 1B shows the ratio of on to off target events (indels) using the indicated pairings. "57618-ELD" and "57629-ELD" refer to ZFNs including the ZFP of Table 1 designated 57618 or 57629 (respectively) fused to a FokI ELD dimerization mutant. "55629-KKR" and "57718-KKR" refer to ZFNs including the ZFP of Table 1 designated 55629 or 57718 (respectively) fused to a FokI KKR dimerization mutant. "57618-nr-5Qabc-ELD," "57629-nr-5Qabc-ELD," "55629-nr-5Qabc-KKR" and "57718-nr-5Qabc-KKR" refer to the ZFNs with the indicated ZFPs (57618, 57629, 55629, and 57718, respectively) and indicated dimerization mutants (ELD or KKR) as well ZFP phosphate contact mutants (nR-5Qabc). "57718-KKR-K525S," "57629-ELD-K525S," "55629-KKR-K525S" and "57618-ELD-K525S" refer to the ZFNs with the indicated ZFPs (57718, 57629, 55629, and 57618, respectively) and indicated dimerization mutants (ELD or KKR) as well FokI phosphate mutants (R416S and K525S). "57618-nr-5Qabc-ELD-K525S," "57692-nr-5Qabc-ELD-K525S," "55629-nr-5Qabc-KKR-K525S" and "57718-nr-5Qabc-KKR" refer to the ZFNs with the indicated ZFPs (57618, 57629, 55629, and 57718, respectively) and indicated dimerization mutants (ELD or KKR) as well a combination of ZFP phosphate contact mutants (nR-5Qabc) and FokI phosphate contact mutants (R416S and K525S).

DETAILED DESCRIPTION

Disclosed herein are compositions and methods for targeted modification of an IL2RG gene, including modification via integration of a corrective SCID-related protein (e.g., IL2RG, RAG1 or RAG2) transgene into a IL2RG gene of cell (e.g., lymphocyte precursors such as CD34+ hematopoietic stem cells). The cells are suitable for infusion into severe combined immunodeficiency (X-SCID or SCID) patients such that subsequent in vivo differentiation of these precursors into cells expressing the functional proteins lacking or deficient in the subject with a SCID disorder is provided by the cell, which cells can treat and/or prevent disease in the recipient SCID patient. Cells comprising an IL2RG transgene are suitable for infusion into X-SCID patients such that subsequent in vivo differentiation of these stem cells into cells that express the functional IL2RG protein treat and/or prevent X-SCID disease in the patient. Similarly, stem cells comprising the RAG1 or RAG2 transgenes following targeted integration into the IL2RG gene as described herein are suitable for infusion into Omenn Syndrome patients such that subsequent in vivo differentiation of these precursors into cells expression the functional Rag1 and/or Rag2 proteins treats and/or prevents disease in an Omenn Syndrome patient. In addition, cells as described herein (populations of cells or cell lines) can be used in vitro to produce proteins from the integrated transgene, which protein can be isolated and used to treat a subject.

Targeted integration of IL2RG, RAG1 or RAG2 (e.g., into intronic regions of IL2RG, RAG1 and/or RAG2 and/or a safe harbor gene) avoids the issues associated with gene therapy methods that involve random integration of IL2RG, RAG1 or RAG2 into the genome as well as methods that involve integration into exons of IL2RG, RAG1 or RAG2. In particular, random integration often results in adverse events due to the partially transcribed upstream region of the locus and, in addition, intronic insertion at the IL2RG, RAG1 or RAG2 locus utilizes the endogenous transcriptional regulatory elements such as native RNA splicing, promoters, and enhancers which least invasively replaces the defective locus with a correct form.

The invention contemplates the integration of a donor comprising any functional IL2RG or Rag protein, including a functional fragment of these proteins such as a partial cDNA comprising exons 2-8 of the IL2RG gene, a splice acceptor sequence and a polyadenylation sequence. Also contemplated is the integration of a donor comprising a full cDNA of RAG1 or RAG2. Targeted integration of the IL2RG donor into intron 1 of the endogenous IL2RG will result in the expression of a wild-type IL2RG or common gamma protein, thus treating or preventing X-SCID. Targeted integration of the RAG1 or RAG2 donor will result in the expression of wild type Rag1 or Rag2, thus treating or preventing Omenn Syndrome.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding domain" is a molecule that is able to bind non-covalently to another molecule. A binding molecule can bind to, for example, a DNA molecule (a DNA-binding protein such as a zinc finger protein or TAL-effector domain protein or a single guide RNA), an RNA molecule (an RNA-binding protein) and/or a protein molecule (a protein-binding protein). In the case of a protein-binding molecule, it can bind to itself (to form homodimers, homotrimers, etc.) and/or it can bind to one or more molecules of a different protein or proteins. A binding molecule can have more than one type of binding activity. For example, zinc finger proteins have DNA-binding, RNA-binding and protein-binding activity. Thus, DNA-binding molecules, including DNA-binding components of artificial nucleases and transcription factors include but are not limited to, ZFPs, TALEs and sgRNAs.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs that dimerize to cleave the target gene.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,585,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo or CRISPR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 8,623,618; 7,888,121; 7,914,796; and 8,034,598, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. Target sites may be any length, for example, 9 to 20 or more nucleotides and length and the bound nucleotides may be contiguous or non-contiguous.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), *Agrobacterium*-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or Cas DNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

"Stemness" refers to the relative ability of any cell to act in a stem cell-like manner, i.e., the degree of toti-, pluri-, or oligopotentcy and expanded or indefinite self-renewal that any particular stem cell may have.

Fusion Molecules

Described herein are compositions, for example nucleases, that are useful for cleavage of a selected target gene (e.g., IL2RG) in a cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding molecules and/or cleavage domain(s). For example, the DNA-binding portion of a naturally-occurring nuclease may be altered to bind to a selected target site (e.g., a single guide RNA of a CRISPR/Cas system or a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). Thus, any nuclease may be used in the practice of the present invention including but not limited to, at least one ZFN, TALEN, meganuclease, CRISPR/Cas nuclease or the like, which nucleases that cleave a target (e.g., IL2RG, RAG, etc.) gene, which cleavage results in genomic modification of the target gene (e.g., insertions and/or deletions into the cleaved gene).

Also described herein are methods to increase specificity of cleavage activity through independent titration of the engineered cleavage half-domain partners of a nuclease complex. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. When used individually or in combination, the methods and compositions of the invention provide surprising and unexpected increases in targeting specificity via reductions in off-target cleavage activity. The nucleases used in these embodiments may comprise ZFNs, TALENs, CRISPR/Cas, CRISPR/dCas and TtAgo, or any combination thereof.

A. DNA-Binding Molecules

The fusion molecules described herein can include any DNA-binding molecule (also referred to as DNA-binding domain), including protein domains and/or polynucleotide DNA-binding domains. In certain embodiments, the DNA-binding domain binds to a sequence comprising 9 to 12 contiguous nucleotides of SEQ ID NO:1 or SEQ ID NO:2.

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG fSEQ ID NO: 24) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Duj on et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et al ((2010)<Genetics epub 10.1534/genetics.110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A ZFP can be operably associated (linked) to one or more nuclease (cleavage) domains to form a ZFN. The term "a ZFN" includes a pair of ZFNs that dimerize to cleave the target gene. Methods and compositions can also be used to increase the specificity of a ZFN, including a nuclease pair, for its intended target relative to other unintended cleavage sites, known as off-target sites (see U.S. patent application Ser. No. 15/685,580). Thus, nucleases described herein can comprise mutations in one or more of their DNA binding domain backbone regions and/or one or more mutations in their nuclease cleavage domains. These nucleases can include mutations to amino acid within the ZFP DNA binding domain ('ZFP backbone') that can interact non-specifically with phosphates on the DNA backbone, but they do not comprise changes in the DNA recognition helices. Thus, the invention includes mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In some aspects, the DNA-binding domain (e.g., ZFP, TALE, sgRNA, etc.) targets an IL2RG or RAG gene. In certain embodiments, the DNA-binding domain targets an intronic region of IL2RG or a RAG gene, for example intron 1 or intron 2.

Selection of target sites (e.g., within an intronic region of IL2RG or a RAG gene); ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding molecule is part of a CRISPR/Cas nuclease system. See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

In some embodiments, the DNA binding molecule is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. Ago-RNA-mediated DNA cleavage could be used to affect a panoply of outcomes including gene knock-out, targeted gene addition, gene correction, targeted gene deletion using techniques standard in the art for exploitation of DNA breaks.

Thus, the nuclease comprises a DNA-binding molecule in that specifically binds to a target site in any gene into which it is desired to insert a donor (transgene), particularly an IL2RG and/or RAG transgene.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, U.S. Pat. Nos. 7,888,121; 8,623,618; 7,888,121; 7,914,796; and 8,034,598 and U.S. Publication No. 20110201055. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., S1 Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,623,618; 7,888,121; 7,914,796; and 8,034,598 and U.S. Publication No. 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

In certain embodiments, the engineered cleavage half domains are derived from FokI and comprise one or more mutations in one or more of amino acid residues 416, 422, 447, 448, and/or 525 (see, e.g., U.S. application Ser. No. 15/685,580) numbered relative to the wild-type full length FokI as shown below:

```
Wild type FokI cleavage half domain
                                 (SEQ ID NO: 21)
QLVKSELEEKKSELRHKLKYVPHEYIELIEIARNSTQDRILEMKVMEFFM

KVYGYRGKHLGGSRKPDGAIYTVGSPIDYGVIVDTKAYSGGYNLPIGQAD

EMQRYVEENQTRNKHINPNEWWKVYPSSVTEFKFLFVSGHFKGNYKAQLT

RLNHITNCNGAVLSVEELLIGGEMIKAGTLTLEEVRRKFNNGEINF
```

These mutations decrease the non-specific interaction between the FokI domain and a DNA molecule. In other embodiments the cleavage half domains derived from FokI comprises a mutation in one or more of amino acid residues 414-426, 443-450, 467-488, 501-502, and/or 521-531. The mutations may include mutations to residues found in natural restriction enzymes homologous to FokI. In certain embodiments, the mutations are substitutions, for example substitution of the wild-type residue with a different amino acid, for example serine (S), e.g. R416S or K525S. In a preferred embodiment, the mutation at positions 416, 422, 447, 448 and/or 525 comprise replacement of a positively charged amino acid with an uncharged or a negatively charged amino acid. In another embodiment, the engineered cleavage half domain comprises mutations in amino acid residues 499, 496 and 486 in addition to the mutations in one or more amino acid residues 416, 422, 447, 448, or 525. In a preferred embodiment, the invention provides fusion proteins wherein the engineered cleavage half-domain comprises a polypeptide in which the wild-type Gln (Q) residue at position 486 is replaced with a Glu (E) residue, the wild-type Ile (I) residue at position 499 is replaced with a Leu (L) residue and the wild-type Asn (N) residue at position 496 is replaced with an Asp (D) or a Glu (E) residue ("ELD" or "ELE") in addition to one or more mutations at positions 416, 422, 447, 448, or 525.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey" mutations (see Guo et al, (2010)*J Mol. Biol.* 400(1):96-107).

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) Sciencexpress 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

In some embodiments, the CRISPR-Cpf1 system is used. The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "'Cas" includes both Cas9 and Cpf1 proteins. Thus, as used herein, a "CRISPR/Cas system" refers both CRISPR/Cas and/or CRISPR/Cpf1 systems, including both nuclease and/or transcription factor systems.

Target Sites

As described in detail above, DNA-binding domains can be engineered to bind to any sequence of choice. An engineered DNA-binding domain can have a novel binding specificity, compared to a naturally-occurring DNA-binding domain.

In certain embodiments, the nuclease(s) target(s) an IL2R2 gene or RAG gene (e.g., RAG1 or RAG2), for example an intron (e.g., intron 1 or intron 2) or an exon (e.g., exon 1) of the gene. In certain embodiments, the nuclease binds to a target site of 9-20 or more nucleotides (contiguous or non-contiguous) within a sequence as shown in Table 2.

In certain embodiments, the nuclease target(s) a "safe harbor" loci such as the AAVS1, HPRT, ALB and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Addition non-limiting examples of suitable target genes include a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAV51) gene, an hypoxanthine phosphoribosyltransferase (HPRT) gene, an albumin gene, a Factor VIII gene, a Factor IX gene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFX5 gene, a FAD2 gene, a FAD3 gene, a ZP15 gene, a KASII gene, a MDH gene, and/or an EPSPS gene. In some aspects, the nuclease(s) binds to and/or cleaves a check point inhibitor gene, for example PD-1, CTLA4, receptors for the B7 family of inhibitory ligands, or cleaves a receptor or ligand gene involved in signaling through LAG3, 2B4, BTLA, TIM3, A2aR, and killer inhibitor receptors (KIRs and C-type lectin receptors), see Pardoll (2012) *Nat Rev Cancer* 12(4):252, an HLA complex gene (class I: HLA-A, HLA-B, HLA-C, HLA-E, HLA-F, HLA-G, B2M; class II: HLA-DMA, HLA-DOA, HLA-DPA1, HLA-DQA, HLA-DRA, HLA-DMB, HLA-DOB, HLA-DPB1, HLA-DQB, HLA-DRB) or TCR; and/or a gene encoding a product involved in the peptide loading process and antigen processing for the HLA complexes (e.g. TAP, tapasin, calreticulin, calnexin, LMP2, LMP7 or Erp57). See, e.g., U.S. Pat. Nos. 8,956,828 and 8,945,868.

Donors

In certain embodiments, the present disclosure relates to nuclease-mediated targeted integration of an exogenous sequence (e.g. a transgene encoding an IL2RG and/or Rag protein, including any functional fragment of an IL2RG and/or Rag protein and/or a donor that corrects a mutant wild-type IL2RG sequence) into the genome of a cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence (e.g., a transgene) flanked by two regions of homology to allow for efficient HDR at the location of interest or can be integrated via non-homology directed repair mechanisms. See, e.g., U.S. Pat. Nos. 9,045,763; 9,005,973 and 7,888,121. Additionally, donor sequences can comprise a vector molecule containing sequences that are not homologous to the region of interest in cellular chromatin. A donor molecule can contain several, discontinuous regions of homology to cellular DNA. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors may be introduced using DNA and/or viral vectors by methods known in the art. See, e.g., U.S. Pat. Nos. 9,005,973; 8,936,936 and 8,703,489. The donor may be introduced into the cell in double- or single-stranded form. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In some embodiments, the SCID-related transgene is integrated into the endogenous locus of the IL2RG gene to correct a mutant version (e.g., in a cell from a SCID patient that is lacking or deficient in a functional version of the SCID-related gene), for instance, an IL2RG transgene is integrated into an endogenous IL2RG gene, for example an intronic region (e.g., intron 1) of a mutant IL2RG associated with X-SCID. In other embodiments, the SCID-related transgene is integrated into the endogenous locus of an IL2RG gene such that a functional IL2RG or RAG protein (RAG1 and/or RAG2) is expressed. Thus, the donor may include any SCID-related protein-encoding sequences that produce a functional protein, including but not limited to full-length SCID-related genes (e.g., IL2RG, RAG1, and/or RAG2), partial (functional) sequences of SCID-related genes (e.g., exons 2-8 of IL2RG, exon 3 of RAG1 or RAG2, etc.) and combinations thereof.

Furthermore, although not required for expression, exogenous sequences may also include transcriptional or translational regulatory or other sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO:22) (from the human HBB gene) and TTTCTCTCCACAG (SEQ ID NO:23) (from the human Immunoglobulin-gamma gene).

The SCID-related transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear or chimeric antigen receptors (CARs)), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) IL2RG and/or RAG gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified cells comprising a SCID-related transgene, namely a transgene that expresses a functional protein lacking or deficient in a SCID in the cell, including cells (e.g., T-cells or stem cells) produced by the methods described herein. The transgene is integrated in a targeted manner into the cell's genome using one or more nucleases. In certain embodiments, the transgene is integrated into IL2RG, for example a mutant IL2RG gene as found in X-SCID patients. In certain embodiments, the transgene comprises a functional RAG gene for treatment and/or prevention of Omenn Syndrome patients. The transgene may be integrated into any intronic or exonic region of IL2RG, for example intron 1 or intron 2. In certain embodiments, the transgene is integrated into or within 5-10 nucleotides on either side of SEQ ID NO:1 or 2. Thus, provided herein are genetically modified cells comprising a SCID-related transgene (that expresses a functional protein lacking or deficient in a SCID) integrated in intron 1 or intron 2 of a SCID-related gene as well as cells descended from these cells that include the genetic modification.

Unlike random integration, targeted integration ensures that the transgene is integrated into a specified gene. The transgene may be integrated anywhere in the target gene. In certain embodiments, the transgene is integrated at or near the nuclease cleavage site, for example, within 1-300 (or any value therebetwen) base pairs upstream or downstream of the site of cleavage, more preferably within 1-100 base pairs (or any value therebetween) of either side of the cleavage site, even more preferably within 1 to 50 base pairs (or any value therebetween) of either side of the cleavage site. In certain embodiments, the integrated sequence comprising the transgene does not include any vector sequences (e.g., viral vector sequences).

Any cell type can be genetically modified as described herein to comprise an IL2RG transgene, including but not limited to cells and cell lines. Other non-limiting examples of IL2RG-transgene containing cells as described herein include T-cells (e.g., CD4+, CD3+, CD8+, etc.); dendritic cells; B-cells; autologous (e.g., patient-derived) or heterologous pluripotent, totipotent or multipotent stem cells (e.g., CD34+ cells, induced pluripotent stem cells (iPSCs), embryonic stem cells or the like). In certain embodiments, the cells as described herein are CD34+ cells derived from an X-SCID patient.

The SCID-related protein-expressing cells as described herein are useful in treating and/or preventing SCID (e.g., X-SCID and/or Omenn Syndrome) in a subject with the disorder, for example, by ex vivo therapies. The nuclease-modified cells can be expanded and then reintroduced into the patient using standard techniques. See, e.g., Tebas et al (2014) New Eng J Med 370(10):901. In the case of stem cells, after infusion into the subject, in vivo differentiation of these precursors into cells expressing the functional IL2RG protein also occurs. Pharmaceutical compositions comprising the cells as described herein are also provided. In addition, the cells may be cryopreserved prior to administration to a patient.

The cells and ex vivo methods as described herein provide treatment and/or prevention of SCID in a subject (e.g., a mammalian subject) and eliminate the need for continuous prophylactic pharmaceutical administration or risky procedures such as allogeneic bone marrow transplants or gamma retroviral delivery. As such, the invention described herein provides a safer, cost-effective and time efficient way of treating and/or preventing SCID.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to SCID patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933,113; 6,979,539; 7,013,219; and 7,163,824, and U.S. Patent Publication No. US-2014-0335063-A1, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357: 455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bohm (eds.) (1995); and Yu et al., Gene Therapy 1:13-26 (1994).

Methods of non-viral delivery of nucleic acids include electroporation, lipofection, microinjection, biolistics, virosomes, liposomes, immunoliposomes, polycation or lipid:nucleic acid conjugates, lipid nanoparticles (LNP), naked DNA, naked RNA, capped RNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc. (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of Felgner, WO 91/17424, WO 91/16024. In some aspects, the nucleases are delivered as mRNAs and the transgene is delivered via other modalities such as viral vectors, minicircle DNA, plasmid DNA, single-stranded DNA, linear DNA, liposomes, nanoparticles and the like.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:15-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, sublingual or intracranial infusion) topical application, as described below, or via pulmonary inhalation. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application, inhalation and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by an AAV, while the one or more nucleases can be carried by mRNA. Furthermore, the different systems can be administered by the same or different routes (intramuscular injection, tail vein injection, other intravenous injection, intraperitoneal administration and/or intramuscular injection. Multiple vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions disclosed herein are for providing therapies for SCID-related disorders (e.g., X-SCID, Omenn Syndrome), for example via the provision of proteins lacking or deficient in a SCID disorder. The cell may be modified in vivo or may be modified ex vivo and subsequently administered to a subject. Thus, the methods and compositions provide for the treatment and/or prevention of a SCID disorder.

Targeted integration of an SCID-related transgene (e.g., IL2RG and/or RAG transgene) may be used to correct an aberrant SCID-related gene, insert a wild type gene, or change the expression of an endogenous gene. For instance, a wild-type transgene encoding IL2RG, which is deficient in X-SCID patients, may be integrated into a cell to provide a cell that produces a functional protein. Similarly, a wild-type transgene encoding a RAG gene (e.g., RAG1 or RAG2), which is deficient in Omenn Syndrome SCID patients, may be integrated into a cell to provide a cell that produces a functional Rag protein. Genomic editing may also include correction of mutations (e.g., point mutations) in a faulty endogenous gene, thereby resorting expression of the gene and treating the disorder.

By way of non-limiting example, the methods and compositions described herein can be used for treatment and/or prevention of SCID.

The following Examples relate to exemplary embodiments of the present disclosure in which the nuclease comprises a zinc finger nuclease (ZFN). It will be appreciated that this is for purposes of exemplification only and that other nucleases can be used, for example TALEN, TtAgo and CRISPR/Cas systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins. For instance, additional nucleases may be designed to bind to a sequence comprising 9 to 12 contiguous nucleotides of SEQ ID NO:1 or 2.

EXAMPLES

Example 1: Zinc Finger Protein Nucleases (ZFN) Targeted to IL2RG

Zinc finger proteins targeted to IL2RG were designed and incorporated into mRNA, plasmids, AAV or adenoviral vectors essentially as described in Urnov et al. (2005) *Nature* 435(7042):646-651, Perez et al (2008) *Nature Biotechnology* 26(7):808-816, and as described in U.S. Pat. No. 6,534,261. Table 1 shows the recognition helices within the DNA binding domain of exemplary IL2RG ZFP DNA-binding domains and the target sites for these ZFPs (DNA target sites indicated in uppercase letters; non-contacted nucleotides indicated in lowercase). Nucleotides in the target site that are contacted by the ZFP recognition helices are indicated in uppercase letters; non-contacted nucleotides indicated in lowercase. TALENs and/or sgRNAs are also designed to the IL2RG sequences shown in Table 2 (e.g., a target site comprising 9 to 20 or more (including 9, 10, 11, 12, 13, 14, 15, 16, 17, 18, 19, 20, 21, or more) nucleotides (contiguous or non-contiguous) of SEQ ID NO:1 or SEQ ID NO:2) following methods known in the art. See, e.g., U.S. Pat. No. 8,586,526 (using canonical or non-canonical RVDs for TALENs) and U.S. Patent Publication No. 20150056705.

All ZFN pairwise combinations (55629 and 57618, 57718 and 57629, 55629 and 57629 and 57718 and 57618) were tested for cleavage activity and found to be active. It will be apparent that these designs may include any linker between any of the finger modules and/or between the ZFP and the cleavage domain, including but not limited to canonical or non-canonical linkers or linkers such as TGEKP (SEQ ID NO:18), TGERG (SEQ ID NO:19), TGSQKP linker (SEQ ID NO:20) (between fingers) and/or linkers between the ZFP and cleavage domain as described in U.S. Pat. No. 9,394,531. See, also, U.S. Pat. No. 8,772,453 and 20150064789.

Furthermore, any of the nucleases (ZFNs, CRISPR/Cas systems and TALENs) can include engineered cleavage domains, for example heterodimers disclosed in U.S. Pat. No. 8,623,618 (e.g., ELD and KKR engineered cleavage domains) and/or cleavage domains with more or more mutations in positions 416, 422, 447, 448, and/or 525 as described in U.S. application Ser. No. 15/685,580. These mutants were used in conjunction with the exemplary ZFP DNA-binding domains described herein.

Example 2: Activity and Specificity of IL2RG-Targeted Nucleases

ZFNs as shown in Table 1 were also evaluated for activity with both on-target and off-target target sites using FokI dimerization mutants and phosphate mutants as described in U.S. application Ser. No. 15/685,580.

The ZFNs were tested in CD34+ in various combinations as shown in FIG. 1. Cryopreserved mobilized peripheral blood (mPB) CD34+ cells were thawed into X-VIVO 10 media containing 100 ng/mL SCF, Flt3L, and TPO and grown for 2 days at 37 C. Cells were then electroporated using a BTX device with ZFN-encoding mRNA at a total concentration of 20 μg/mL or 40 μg/mL. Cells were allowed to recover for 1 additional day in culture before harvesting for genomic DNA and indel (insertions and/or deletions via NHEJ) analysis by next generation sequencing.

As shown in FIG. 1, all ZFNs were active at the intended target site (on-target) and all exhibited higher activity at the on-target site than at the off-target sites. The combination with the highest ratio of on- to off-target activity was 57718-nR-5Qabc-KKR-K525S and 57629-nR-5Qabc-ELD.

Thus, the nucleases with FokI mutants (dimerization and/or phosphate contacts) targeted to IL2RG were all capable of cleaving the target gene with high specificity.

TABLE 1

IL2RG Zinc finger proteins recognition helix designs

| | Design | | | | | |
|---|---|---|---|---|---|---|
| SBS # | F1 | F2 | F3 | F4 | F5 | F6 |
| 55629 | QSGNLAR (SEQ ID NO: 3) | QSGDLTR (SEQ ID NO: 4) | RSDHLSQ (SEQ ID NO: 5) | QSNGLTQ (SEQ ID NO: 6) | TRTVLMN (SEQ ID NO: 7) | QNATRIN (SEQ ID NO: 8) |
| 57618 | TSGNLTR (SEQ ID NO: 9) | QSNDLNS (SEQ ID NO: 10) | YQGVLTR (SEQ ID NO: 11) | RTDNLES (SEQ ID NO: 12) | RSDHLSQ (SEQ ID NO: 5) | RRDNRDT (SEQ ID NO: 13) |
| 57718 | LQSNLNR (SEQ ID NO: 14) | QSGDLTR (SEQ ID NO: 4) | RSDHLSQ (SEQ ID NO: 5) | RKDALPT (SEQ ID NO: 15) | TTTVLRN (SEQ ID NO: 16) | QNATRIN (SEQ ID NO: 8) |
| 57629 | TSGNLTR (SEQ ID NO: 9) | QSNDLNS (SEQ ID NO: 10) | YQGVLTR (SEQ ID NO: 11) | RLDNLHP (SEQ ID NO: 17) | RSDHLSQ (SEQ ID NO: 5) | RRDNRDT (SEQ ID NO: 13) |

TABLE 2

Target Sites of zinc finger proteins

| SBS # | Target site |
|---|---|
| 55629 | ttACAATCATGTGGGCAGAAttgaaaag (SEQ ID NO: 1) |
| 57618 | gcCAGTGGCAGGCACCAGATctctgtac (SEQ ID NO: 2) |
| 57718 | ttACAATCATGTGGGCAGAAttgaaaag (SEQ ID NO: 1) |
| 57629 | gcCAGTGGCAGGCACCAGATctctgtac (SEQ ID NO: 2) |

Example 3: Methylcellulose Assay on Nuclease-Modified CD34+ Cells

Differentiation of the CD34+ cells as treated in Example 2 is analyzed by assay of colony types arising from Methocult-induced differentiation: colony-forming units, erythroid ("CFU-E"); burst-forming units, erythroid ("BFU-E"); colony-forming units, granulocyte/macrophage ("CFU-GM") and colony-forming units; granulocyte/erythrocyte/monocyte/macrophage ("CFU-GEMM") using standard methodology as previously described (Genovese et al. (2014) *Nature;* 510(7504):235-40). In short, CD34+ cells are genome modified, allowed to recover in vitro, then plated in methylcellulose medium and allowed to differentiate for 2 weeks before colonies are analyzed.

IL2RG modification as described herein does not significantly impair CD34+ cells.

Example 4: Targeted IL2RG Donor Insertion

Targeted integration into the IL2RG locus is also performed. Exemplary IL2RG and/or RAG donor constructs as shown in U.S. Patent Publication 20160030477 are integrated into the IL2RG of CD34+ cells using the nucleases described herein.

IL2RG expression in cell lines is rescued by nuclease-mediated introduction of a corrective IL2RG transgene using nucleases as described herein, including at by rescuing IL2RG expression to levels comparable to endogenous levels.

Example 5: Ex Vivo Methods

The genetically modified cells, particularly CD34+ HSPCs obtained from X-SCID or Omenn Syndrome subjects (patient-derived CD34+ cells) as previously described (Aiuti et al. (2013) *Science* 341, 1233151), expressing IL2RG or RAG1 as described herein are administered to X-SCID or Omenn Syndrome patients, respectively as previously described (Aiuti et al. ibid).

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A T-cell or a stem cell comprising one or more insertions and/or deletions in an endogenous IL2RG gene made by a zinc finger nuclease comprising a pair of zinc finger nucleases, each zinc finger nuclease cleavage domain and a zinc finger protein (ZFP) designated 55629, 57618, 57718 or 57629 that binds to a target site comprising 9 or more nucleotides of SEQ ID NO:1 or SEQ ID NO:2, wherein the zinc finger protein comprises 6 fingers ordered F1 to F6, each finger comprising a recognition helix region as shown in the following Table:

|       | F1                    | F2                    | F3                    |
|-------|-----------------------|-----------------------|-----------------------|
| 55629 | QSGNLAR (SEQ ID NO:3) | QSGDLTR (SEQ ID NO:4) | RSDHLSQ (SEQ ID NO:5) |
| 57618 | TSGNLTR (SEQ ID NO:9) | QSNDLNS (SEQ ID NO:10)| YQGVLTR (SEQ ID NO:11)|
| 57718 | LQSNLNR (SEQ ID NO:14)| QSGDLTR (SEQ ID NO:4) | RSDHLSQ (SEQ ID NO:5) |
| 57629 | TSGNLTR (SEQ ID NO:9) | QSNDLNS (SEQ ID NO:10)| YQGVLTR (SEQ ID NO:11)|

|       | F4                    | F5                    | F6                    |
|-------|-----------------------|-----------------------|-----------------------|
| 55629 | QSNGLTQ (SEQ ID NO:6) | TRTVLMN (SEQ ID NO:7) | QNATRIN (SEQ ID NO:8) |
| 57618 | RTDNLES (SEQ ID NO:12)| RSDHLSQ (SEQ ID NO:5) | RRDNRDT (SEQ ID NO:13)|
| 57718 | RKDALPT (SEQ ID NO:15)| TTTVLRN (SEQ ID NO:16)| QNATRIN (SEQ ID NO:8) |
| 57629 | RLDNLHP (SEQ ID NO:17)| RSDHLSQ (SEQ ID NO:5) | RRDNRDT (SEQ ID NO:13)| and further wherein the pair of zinc finger nuclease comprises 55629 and 57618; 57718 and 57629; 55629 and 57629; or 57718 and 57618.

2. The cell of claim 1, wherein the insertion and/or deletion inactivates the endogenous IL2RG gene.

3. The cell of claim 1, wherein an exogenous sequence is inserted into the endogenous IL2RG gene.

4. The cell of claim 3, wherein the exogenous sequence comprises a transgene that encodes an IL2RG or RAG polypeptide.

5. The cell of claim 3, wherein the endogenous IL2RG gene is a mutant gene and the exogenous sequence comprises a sequence that corrects the mutation in the endogenous IL2RG gene such that a functional IL2RG protein is expressed from the cell.

6. The cell of claim 1, wherein the pair of zinc finger nucleases comprises 57718 and 57629.

7. The cell of claim 1, wherein the nuclease is introduced into the cell as a polynucleotide.

8. The cell of claim 7, wherein the polynucleotide is mRNA, a viral vector or a non-viral vector.

9. The cell of claim 1, wherein the viral vector is an adeno-associated viral vector (AAV).

10. The cell of claim 1, wherein the cleavage domain comprises an engineered FokI cleavage domain.

11. The cell of claim 1, wherein the cell is a stem cell.

12. The cell of claim 11, wherein the stem cell is a hematopoietic stem cell or an induced pluripotent stem cell (iPSC).

13. A method of making a hematopoietic stem cell of claim 1, the method comprising introducing the nuclease into the cell wherein the nuclease cleaves the endogenous IL2RG gene such that following cleavage, the one or more insertions and/or deletions are introduced into the endogenous IL2RG gene.

14. The method of claim 13, further comprising introducing an exogenous sequence into the cell such that, following cleavage, the endogenous sequence is introduced into the genome of the cell.

15. A pharmaceutical composition comprising the cell of claim 1.

16. The pharmaceutical composition of claim 15, further comprising genetically modified cells described from the cell, wherein the genetically modified cells comprise the one or more insertions and/or deletions.

17. A method of treating or preventing a SCID-related disorder in a subject, the method comprising introducing into the subject the pharmaceutical composition of claim 15 into the subject.

18. The method of claim 17, wherein the SCID-related disorder is X-SCID or Omenn Syndrome.

* * * * *

SEQUENCE LISTING

```
<160> NUMBER OF SEQ ID NOS: 24

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttacaatcat gtgggcagaa ttgaaaag                                        28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gccagtggca ggcaccagat ctctgtac                                        28

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Gly Asn Leu Ala Arg
1               5

<210> SEQ ID NO 4
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 4

Gln Ser Gly Asp Leu Thr Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Asp His Leu Ser Gln
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Asn Gly Leu Thr Gln
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Arg Thr Val Leu Met Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Asn Ala Thr Arg Ile Asn
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Ser Gly Asn Leu Thr Arg
1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Asn Asp Leu Asn Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Gln Gly Val Leu Thr Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Thr Asp Asn Leu Glu Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Asp Asn Arg Asp Thr
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Gln Ser Asn Leu Asn Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 15

Arg Lys Asp Ala Leu Pro Thr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Thr Thr Val Leu Arg Asn
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Leu Asp Asn Leu His Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gly Glu Lys Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Gly Glu Arg Gly
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Gly Ser Gln Lys Pro
1               5

<210> SEQ ID NO 21
<211> LENGTH: 196
<212> TYPE: PRT
```

```
<213> ORGANISM: Unknown
<220> FEATURE:
<223> OTHER INFORMATION: Description of Unknown:
      Wild-type FokI cleavage half-domain

<400> SEQUENCE: 21

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 22
<211> LENGTH: 25
<212> TYPE: DNA
<213> ORGANISM: Homo sapiens

<400> SEQUENCE: 22
ctgacctctt ctcttcctcc cacag                                           25

<210> SEQ ID NO 23
<211> LENGTH: 13
<212> TYPE: DNA
<213> ORGANISM: Homo sapiens

<400> SEQUENCE: 23
tttctctcca cag                                                        13

<210> SEQ ID NO 24
<211> LENGTH: 9
<212> TYPE: PRT
<213> ORGANISM: Unknown
<220> FEATURE:
<223> OTHER INFORMATION: Description of Unknown:
      homing endonuclease
```

```
<400> SEQUENCE: 24

Leu Ala Gly Leu Ile Asp Ala Asp Gly
1               5
```